United States Patent [19]

Smith, III et al.

[11] 4,029,012

[45] June 14, 1977

[54] TWO-PART INKLESS APPLICATOR FOR FINGERPRINTS

[75] Inventors: Jay Smith, III, Pacific Palisades; Virgle L. Hedgcoth, Santa Monica, both of Calif.

[73] Assignee: Identicator Corporation, San Bruno, Calif.

[22] Filed: Dec. 18, 1975

[21] Appl. No.: 642,165

[52] U.S. Cl. .............................. 101/368; 118/31.5; 118/46; 283/7
[51] Int. Cl.² ..................... B41K 1/00; B42D 15/00
[58] Field of Search .................. 101/327, 333, 368; 283/7, 8, 9; 40/2 R, 2.2; 118/31.5, 46, 500; 427/1, 150; 401/283; 106/21

[56] References Cited

UNITED STATES PATENTS

| | | | |
|---|---|---|---|
| 1,408,389 | 2/1922 | Nordin | 101/111 |
| 2,198,802 | 4/1940 | Brady | 283/7 |
| 2,235,632 | 3/1941 | Heinecke | 106/21 |
| 2,299,652 | 10/1942 | Rahn | 118/31.5 |
| 2,505,487 | 4/1980 | Green | 427/150 |
| 2,857,839 | 10/1958 | Jamieson | 101/327 X |
| 2,900,902 | 8/1959 | Becker | 101/327 X |
| 2,978,352 | 4/1961 | Clarke | 427/150 |
| 3,055,297 | 9/1962 | Leeds | 101/327 X |
| 3,158,094 | 11/1964 | Harris et al. | 101/327 |
| 3,342,911 | 9/1967 | Funahashi | 101/327 X |
| 3,402,663 | 9/1968 | Funahashi | 101/327 |
| 3,432,446 | 3/1969 | Coppeta | 101/327 X |
| 3,442,209 | 5/1969 | Funahashi | 101/327 |
| 3,447,818 | 6/1969 | De Pizzol | 283/7 |
| 3,478,682 | 11/1969 | Funahashi | 101/327 |
| 3,653,945 | 4/1972 | Davis et al. | 427/150 |
| 3,755,517 | 8/1973 | Clancy et al. | 101/333 X |
| 3,832,947 | 9/1974 | Funahashi | 101/327 |
| 3,851,619 | 12/1974 | Cofield, Jr. | 118/31.5 |
| 3,855,925 | 12/1974 | Funahashi | 101/333 |
| 3,960,632 | 6/1976 | Gaines et al. | 118/31.5 |

FOREIGN PATENTS OR APPLICATIONS 428,386  5/1935  United Kingdom ................... 427/1

*Primary Examiner*—Edgar S. Burr
*Assistant Examiner*—Paul J. Hirsch
*Attorney, Agent, or Firm*—Jackson & Jones Law Corporation

[57] ABSTRACT

The present invention comprises an apparatus for inkless fingerprinting directly on a medium, such as a check. The apparatus can include a stamp housing having a replaceable cartridge with a pair of reservoir resilient foam cell pads having a semi-sealed surface. One of the pads will contain a liquid developer solution, for example, a water soluble inorganic compound; while the other pad will contain a liquid reagent solution, for example, a water soluble inorganic compound which can react with the liquid developer solution to deposit a non-soluble colorant precipitate. Advantageously, the liquid developer solution will include a carrier solvent that is relatively non-evaporative over the life of the applicator, and has a viscosity value that permits the liquid developer solution to be deposited on a porous medium surface and maintain a coating having only sufficient thickness above the medium surface to contact and adhere to substantially only the ridge pattern of a finger. A second liquid reagent solution will be contained in the other pad and has a relatively lower viscosity to permit the reagent solution to be absorbed to a greater degree into the porous medium.

45 Claims, 10 Drawing Figures

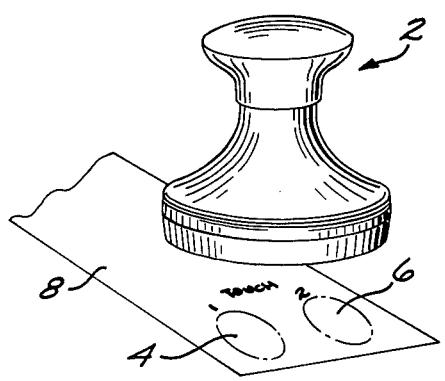
FIG. 1
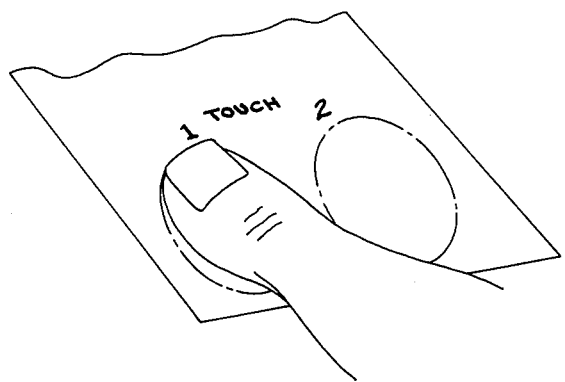
FIG. 2
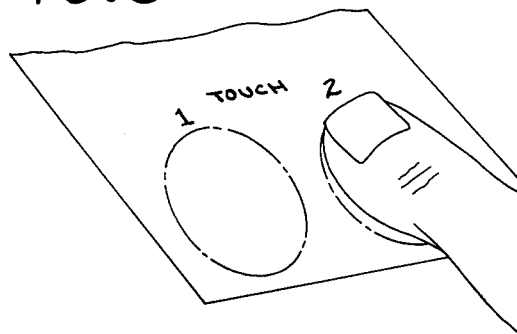
FIG. 3
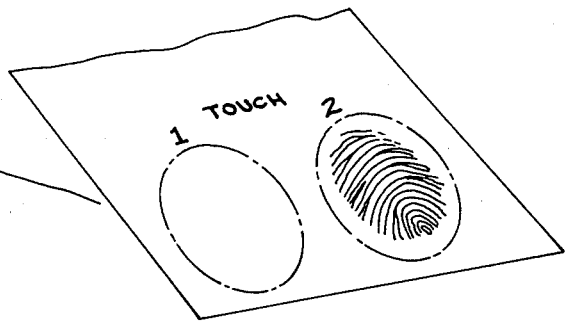
FIG. 4
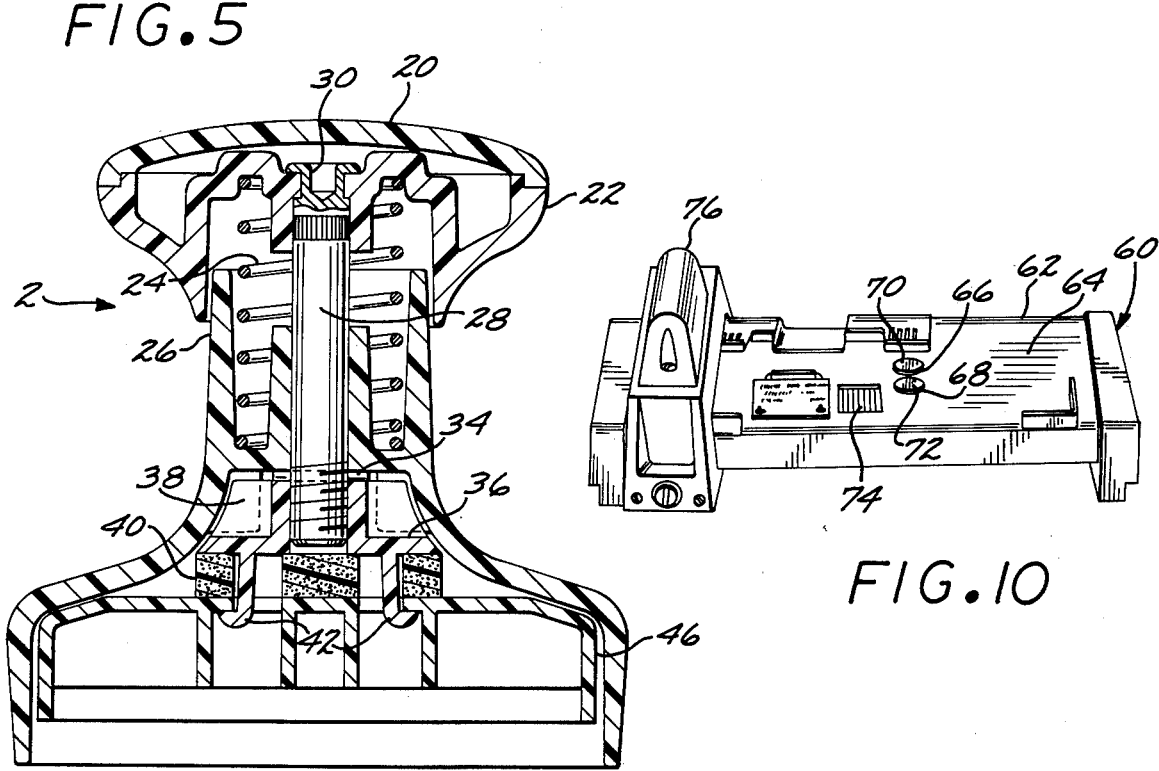
FIG. 5
FIG. 10

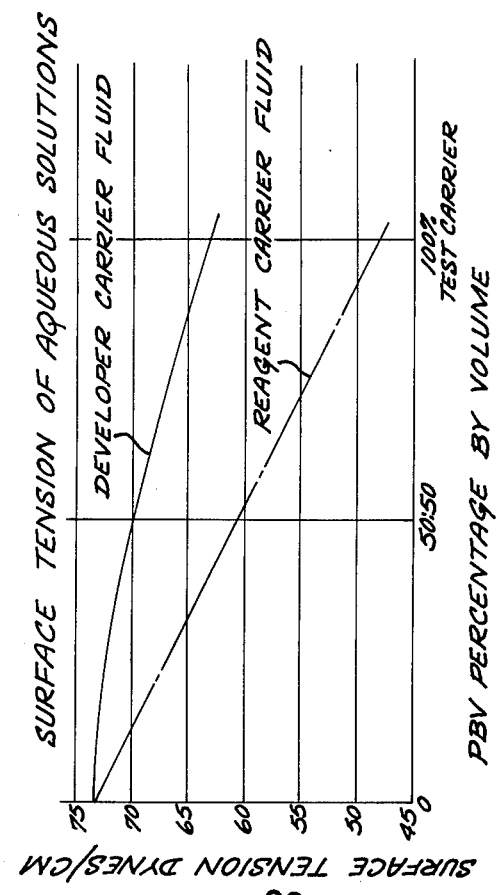
FIG. 7
FIG. 8
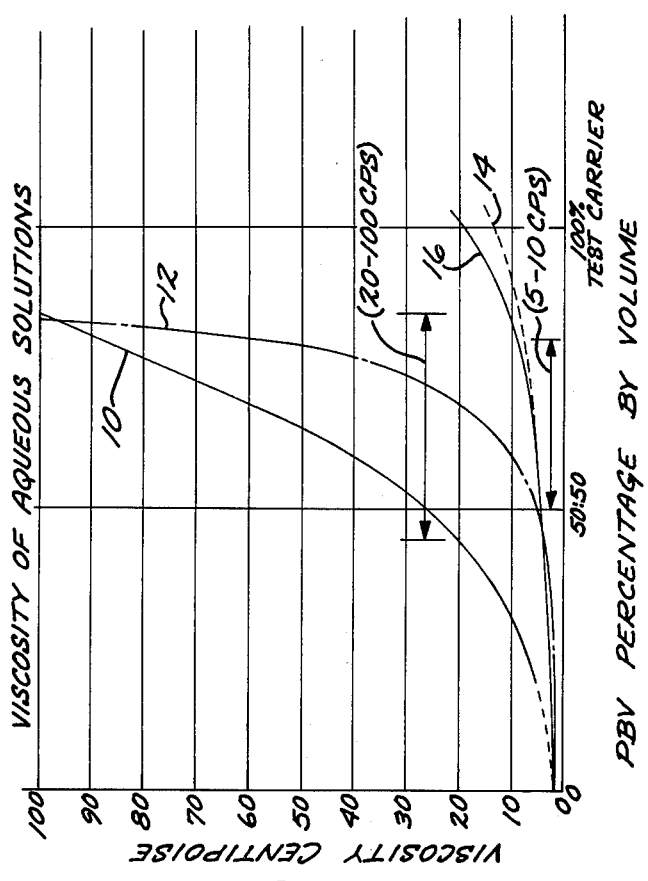
FIG. 9
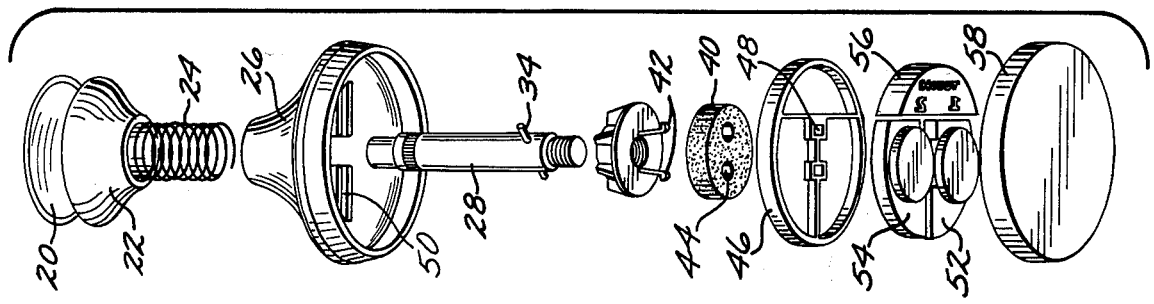
FIG. 6
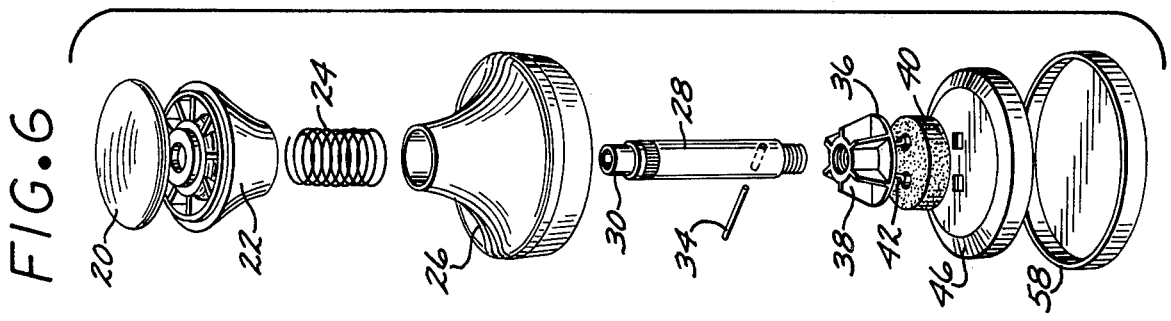

TWO-PART INKLESS APPLICATOR FOR FINGERPRINTS

BACKGROUND OF THE INVENTION

1. Field of the Invention

The present invention is directed to an improved inkless fingerprint identification system, and more particularly, to a method and apparatus which permits the medium to directly receive in two segregated areas the proper thickness of liquid developer solution and liquid reagent solution so that a person can imprint his fingerprint by only contacting the medium.

2. Description of the Prior Art

Although there are other methods of identifying individuals, it has become readily apparent that fingerprints provide a unique and absolute means of identification that does not require cooperation from the subject. Fingerprint identification is an exacting science since two impressions of even the same fingerprint can appear different due to variations in inking, pressure, ink migration and changes in the finger itself with time. To determine and exact correspondence, a trained fingerprint technician will compare the pattern of ridge endings and ridge bifurcations (minutiae) which are invariant with time on each person's fingerprint. For a further discussion of the characteristics of fingerprint classification, reference is made to U.S. Pat. No. 3,419,287.

The prior art has recognized that the key to any viable fingerprint identification system requires a clear distinct print pattern with a minimum of inking migration between associate ridges. An additional requirement for any voluntary print identification system, such as to be utilizied commercially with checks and the like, is that it be inoffensive to the person whose fingerprint is being obtained. A prime offense to persons has been the necessity to utilize an ink that would stain the hands of the person, such as a fingerprint kit utilizing a pair of pads for applying ink and then removing the ink from the finger as disclosed in U.S. Pat. No. 3,318,282.

The prior art has directed a considerable amount of effort to try and develop a successful inkless fingerprinting system. One commercial approach has been to utilize a fine magnetizable powder that will adhere to the moisture of a fingerprint on a substrate surface, see U.S. Pat. No. 3,831,552.

U.S. Pat. No. 3,851,619 discloses an inkless fingerprinting system which includes an aerosol dispenser with a metering valve to control the dryness of a reagent solution at the point of impact on the print surface. The reagent solution having the solvent removed prior to the contact of the developer coated finer and the developer being a ferric salt, such as ferric chloride, with the respective materials being kept in an airtight enclosure. The problem with applying a developer solution to the ridge pattern of the fingerprint is recognized and purportedly solved by the use of a specific rigid pad with a spaced permeable membrane.

In applying the active materials of the reagent solution and the developer solution in an inkless printing system, there is a need to prevent, or minimize, migration or bleeding, not only with the initial contact of the fingerprint to the surface, but also over a period of time. Quite frequently, prints were developed that were acceptable for instantaneous recognition, but would deteriorate and limit the use of the print as a means of identification, for example, during a time period associated with clearing a check, or in the case of using the check as evidence in apprehending a forger. Conversely, other systems would permit a print to develop slowly over a period of time, but would not permit the print to be perceptible to an observer to determine if the print was immediately smudged, or blurred, at the time of taking the print.

Other approaches in the prior art can be found in the following patents: U.S. Pat. No. 2,082,735; U.S. Pat. No. 2,104,586; U.S. Pat. No. 2,198,802; U.S. Pat. No. 3,083,682; U.S. Pat. No. 3,258,277; U.S. Pat. No. 3,447,818; U.S. Pat. No. 3,694,240; and U.S. Pat. No. 3,584,958.

Commercially, various systems have been offered to the public, such as an ultra-violet ink pad, which permits the finger to contact the pad to apply the ink on the finger to a check. This system requires an ultra-violet light to determine if a good print has been taken.

Chemically impregnated stickers have also been provided for attachment to a document. A complementary chemically impregnated cardboard pad is provided for the finger to contact the cardboard pad, and then subsequently, contact the sticker to develop a fingerprint. Problems exist in both the quality of the fingerprint and in the removability of the sticker, for example, when using an automatic check reading machine.

Recently, the Federal Bureau of Investigation authorized a study on fingerprint ink, "The Influence of Ink on the Quality of Fingerprint Impressions" by R.T. Moore, NBSIR 74-627 (1974) and concluded that the thickness and uniformity of the ink film rolled on the glass plate is a major factor in producing impressions capable of being utilized with automatic fingerprint reading equipment. The study suggested that an ink film thickness of 2 micrometers was desirable and that the apparent viscosity of slipperiness of the ink was not as important as the volume of ink dispensed.

Apart from the field of fingerprinting, the paper industry has investigated the porosity of paper from both an empirical and theoretical approach, see "The Porous Structure of Paper", by H.F. Rance, Tenth Symposium of the Colston Research Society, Butterworth's Scientific Publication, London, Eng. (1958); "Capillary Penetration of Fibrous Materials", by R. L. Peck, Jr. et al. 1934, Industrial and Engineering Chemistry, Vol. 6, No. 2, page 85, and the Technical Association of the Pulp and Paper Industry standards, T 431-ts-65, T432ts-64, T 433-m-44 and T 433-os-74. The information from the paper industry is simply provided as explanatory of the states of that art.

Many of the systems suggested in the prior art, suffer from the disadvantage of permitting an element of discretion to occur in the degree of coating of the finger by contact with an impregnated pad. If the chemical saturates the finger ridge pattern, a blurred print will occur. If an inadequate amount of material is applied to the finger ridge pattern, a fragmented fingerprint will be produced. An additional factor of sanitation in commercial establishments is also present when a large number of customers are forced to utilize the same pad.

There is a need in the prior art to provide a positive inkless fingerprinting identification system that isolates the person whose print is to be taken from the source of the reagents and developer chemical and also insures a quality recorded print. The prior art has failed to provide a controlled repeatable thickness of developer solution with an optimized integration of a reagent solution with the medium to insure a permanent clear print. Ideally, the system must be durable, convenient to the customer and not add any additional time to a purchase transaction involving a check. Also, the system must be capable of repeated use within a minimal cost.

SUMMARY OF THE INVENTION

The present invention is directed to an apparatus and method for repetitively preparing mediums, such as checks, paper documents and the like, for use in a two-step printing process to retain identifiable fingerprints on the medium. The apparatus includes a housing which can movably mount a pair of reservoir resilient foam cell pads having respective semi-sealed surfaces for pressure contact with the surface of the medium. Additionally, a printing pad with an appropriate indicia can also be mounted on the housing for direct printing of either instructions, or other information on the medium. The housing can take the form of a hand stamp, and in the preferred embodiment, has a peripheral support member which can maintain the respective resilient pads off of any support surface.

Optimumly, the pads will be mounted on a replaceable cartridge and carry sufficient developer and reagent solutions to develop a large number of prints over a considerable period of time. A first liquid developer solution having a viscosity value in the range of 20 centipoise (cps) to 100 centipoise (cps) can be obtained in one pad and that pad, upon pressure contact with the medium surface, is capable of depositing a quantity of the first liquid developer solution on the medium. The quantity of developer solution absorbed, depending on its relative viscosity and penetration rate, provides a coating on the medium surface having only sufficient thickness to permit the contacting and adhering of the developer solution to substantially only the ridge pattern of the finger. The other resilient pad contains a liquid reagent solution having a lower viscosity and a higher penetration rate to permit the reagent solution to be applied and absorbed to a greater degree into the medium than the developer solution upon pressure contact. The reagent liquid solution is capable of chemically interacting with the developer solution to provide an immediate colorant precipitate, or indicia, that will not migrate, or bleed, over an acceptable time period.

The respective liquid developer solution and liquid reagent solution can be water soluble inorganic compounds which can react to form a non-soluble colorant precipitate.

In one preferred system, the liquid developer solution is a ferric salt solution, such as a mixture of hydrated ferric chloride, distilled water and glycerine. The liquid reagent solution can be a quinolinol derivative or can be a mixture of potassium hexacyanoferrate (II) trihydrate or sodium hexacyanoferrate (II) decahydrate and distilled water and ethylene glycol. Both the liquid developer solution and the liquid reagent solution are relatively non-evaporative in ambient conditions over the projective time of life of the cartridge. An advantage of the present invention is the simultaneous coating of the medium with both the reagent and developer solutions. A further advantage of the present invention is in providing solvent material which is non-evaporative and of the proper viscosity and penetration rate to control both the coating of the ridge pattern and the migration, or bleed rate, between the inter-mixed liquid developer and reagent solutions on the medium. The use of replaceable cartridges further optimize the commercial advantages of the present invention. Other forms of inorganic/inorganic; inorganic/organic and pH sensitive systems can be utilized within these design parameters.

The features of the present invention which are believed to be novel are set forth with particularity in the appended claims. The present invention, both as to its organization and manner of operation, together with further objects and advantages thereof, may best be understood by reference to the following description, taken in connection with the accompanying drawings.

BRIEF DESCRIPTION OF THE DRAWINGS

FIG. 1 is a perspective view of the present invention after depositing the developer and reagent solution on a medium ;

FIG. 2 is a perspective view of a step in developing a fingerprint;

FIG. 3 is perspective view of another step in developing a fingerprint;

FIG. 4 is a perspective view of a developed fingerprint on the medium;

FIG. 5 is a cross-sectional view of one embodiment of the present invention applicator;

FIG. 6 is a topside exploded perspective view of the present invention;

FIG. 7 is a bottom side exploded perspective view of the present invention;

FIG. 8 is a graph of viscosity versus carrier mixture ratios;

FIG. 9 is a graph of surface tension versus carrier mixture ratios; and

FIG. 10 is a perspective view of a printing machine embodiment of the present invention.

BRIEF DESCRIPTION OF THE PREFERRED EMBODIMENT

The following description is provided to enable any person skilled in the field of fingerprint identification to make and use the invention and sets forth the best modes contemplated by the inventors of carrying out their invention. Various modifications, however, will remain readily apparent to those skilled in the art, since the generic principles of the present invention have been defined herein specifically to provide a commercial fingerprint stamp apparatus that can be manufactured in a relatively economical manner and is adaptable for receiving replaceable cartridges. It should be realized also that the generic principles of the present invention are equally applicable with minor modifications of the applicator to producing developed patterns of other parts of the body, such as palm prints or foot prints. Likewise, it is also possible to reproduce an image from a mechanical object.

Referring to FIG. 1, the fingerprint applicator apparatus 2 applies a first developer solution 4 and a second liquid reagent solution 6 on a medium 8, such as a check. The terms developer and reagent have been selected simply for convenience in understanding the specifications of the present invention. It should be fully understood that the respective active chemical ingredients, subsequently described, can in many cases be carried by the inert carrier fluid of either the developer or reagent to develop a fingerprint. The developer solution 4, when utilized as the first fluid to be contacted by a ridge pattern of a fingerprint, must maintain sufficient film thickness on the surface of the medium to contact and adhere to substantially only the ridge pattern of a finger when the finger is applied to the coated medium. The fingerprint applicator apparatus 2 also applies a quantity of the second liquid reagent solution 6 to the medium 8 in a second separate area on the check. The second reagent solution 6 is applied and immediately absorbed into the medium upon pressure contact of the stamp. The components of the reagent liquid are capable of chemically interacting with components of the developing solution to provide a colorant product, such as a precipitate. In its principle use, both the developer solution and the reagent solution active components and product must be non-toxic and non-irritant to humans.

The first liquid developer solution includes both an active reagent, or chemical compound, and an appropriate inert carrier fluid. Since the present invention is designed to deposit the respective active chemicals and their appropriate inert carrier solutions onto a relatively porous medium, such as a check, document, paper or otherwise, it is important that sufficient thickness of the developer solution be maintained above the medium surface to contact and adhere to substantially only the ridge pattern of the finger. If the developer solution is excessive, it can saturate the finger ridge pattern and a blurred print will occur. If an inadequate amount of material is applied to the finger ridge pattern, a fragmented fingerprint will be produced. Thus, it is important, for at least a short period of time after the depositing of the developer solution 4, e.g., 5–60 seconds, that a controlled thickness be maintained above the surface of the medium. This is accomplished in the present invention by a careful selection of the viscosity and penetration rates of primarily, the inert carrier fluid, taking into consideration the hydraulic pressure generated during depositing and the necessary active life time requirements of the solutions exposed to ambient conditions. It has been found that a first liquid developer solution 4 having a total viscosity value in the range of 20 cps to 100 cps with a steady state penetration rate of approximately 1 to 2 microns/sec, will maintain a sufficient thickness for the necessary time period when deposited by a resilient pad.

The second reagent solution likewise utilizes an inert or neutral carrier medium and an active component in the first developer solution to provide an immediate colorant product. The necessity of an immediate colorant product is to insure that an adequate fingerprint is taken which can be visually checked by, for example, a clerk at a supermarket. The second liquid reagent solution when applied to the medium must be absorbed into the medium to insure that the developed fingerprint will be integral with the medium, while at the same time, minimizing any migration, or bleeding, of the fingerprint ridge characteristics both during the initial contact and over the life of the print. Since the colorant product, or precipitate, resulting from the chemical reaction of the developer solution with the reagent solution is in the matrix structure of the medium, it is possible to insure that the resultant fingerprint cannot be erased, or removed, without actually destroying the medium surface itself. This is of particular importance with checks that are sometimes subjected to abrasion during monitoring with an automatic check reading machine.

Since the actual developing of a fingerprint will occur in a commercail enviroment with a degree of variability in time application, it is important that the second liquid reagent solution 6 have a viscosity below 20 cps, and preferably, in the range of 5 to 10 cps with a steady state isobaric penetration rate at atmospheric pressure of approximately 6 to 10 microns/sec to permit the reagent solution to be applied and immediately absorbed to a greater degree into the medium, than the developer solution 4. By adhering to these parameters, a colorant product representative of the fingerprint ridge pattern will be integrally developed in the medium and a minimum amount of migration, or bleeding, will occur and finally a minimal amount of residue of, for example, a colorant precipitate, will be left on the finger. Thus, a truly inkless fingerprint system will be provided that will be both simple and free of any messiness to the customer.

As mentioned earlier, the inert carrier medium can be respectively, glycerine or ethylene glycol and an important feature of the carrier medium is that it will be relatively non-evaporative over the life of the stamp. For this reason, solvents that are evaporative, such as alcohol, are undersirable.

Equally important features in the selection of the inert carrier mediums are the penetration rate and the viscosity. The identification apparatus of the present invention is designed to be used with commercial paper having a porous surface, such as a check and the like. From a theoretical viewpoint, the medium will be primarily paper and can be treated as a parallel bundle of smooth walled capillaries with the derived isobaric steady state rate of liquid penetration parallel to the fibers being established by the following equation:

$$dH/dt = \frac{\rho \, r \cos \theta}{4 \, \eta \, H}$$

wherein
H is the capillary column height (average);
$\rho$ is surface tension of the solid/liquid system;
$\eta$ is the viscosity of the liquid;
$\theta$ is the contact angle of liquid to solid;
r is the average capillary radius.

The significance of the equation for the purposes of the present invention is that the steady state rate of penetration varies directly as a function of the surface tension and inversely, as a function of the viscosity of the liquid. Thus, the necessary criterion for wetting of a solid by a liquid is that the surface energy of the solid be higher than that of the liquid, see Journal Colloid Science, Volume 7, P-109 (1952).

An important additional consideration to take into account is the transient hydraulic pressure effect of the delivery apparatus on the penetration rate. When the foam pads are compressed against the medium surface, it is believed that the liquid depoisited on the medium probably experiences an initial supra-atmospheric pressure surge, and possibly, a subsequent sub-atmospheric pressure surge. It is believe that the hydraulic pressure effect directly effects the penetration rates, and accordingly, this effect was considered in empirically deriving the desired viscosity ranges of the present invention set forth herein.

For a liquid to wet a fibrous capillary type of medium, such as paper, it is necessary for the surface tension of the medium to be larger than the combined solid-liquid surface tension and the actual liquid surface tension. Generally, paper can be treated as having a medium energy surface with a surface tension in the order of 50–100 dynes/cm. By the careful selection of the parameters of both the developer solution and the reagent solution components, it is possible to control the surface tension and viscosity so that their penetration rates will be at an optimum. In this regard for the developer solution 4, it is desirable that the penetration rate be relatively slow so that it is possible to have a controlled thickness maintained on the surface of the medium for the desired time period. Accordingly, the developer solution will have a low surface tension for the solid-liquid interface while it will have a relatively high liquid viscosity.

Conversely, in the liquid reagent solution, the respective viscosity and surface tension levels are controlled so that the penetration rate is relatively rapid. Accordingly, a surface tension of the solid-liquid interface will be relatively high while the viscosity of the liquid will be relatively low in the reagent solution as compared to the parameters of the developer solution. With a high penetration rate for the reagent solution, the subsequent chemical reaction will occur in the capillary matrix of the medium and not on the surface of the medium, thereby avoiding any colorant product adhering on the finger, and further, minimizing any bleeding, or migration problems in the developed fingerprint.

A steady state penetration rate for a liquid developer solution which maintains a desirable controlled thickness for a time period of approximately 20 seconds, was empirically found to be within the range of 1 to 2 microns/sec. An actual steady state penetration rate was measured at 1.7 microns/sec for a volume mixture of 33 percent saturated hydrated ferric chloride at approximately 20° C with a volume mixture of 67 percent glycerine.

The desired penetration rate for a liquid reagent solution is approximately in the range of 6 to 10 microns/sec for a volume mixture of approximately 33 percent aqueous sodium ferrocyanide solution and 67 percent ethylene glycol. An actual steady state penetration rate was measured at 8 microns/sec. The aqueous sodium ferrocyanide having a mixture ratio of 10 grams to 50 milliliters of the distilled water. The actual steady state penetration rate will vary depending on the surface tension, and viscosity of the solution and the characteristics of the particular paper.

The present derivations have been directed at a range of normal commercial paper, such as checks and the like, in developing the present invention. In measuring the isobaric steady state rate of penetration, that is the rate of penetration subsequent to any hydraulic pressure surges generated during depositing of the liquids, the procedures suggested in the Peck, Jr. et al. article on "Capillary Penetration of Fibrous Materials" was utilized on a controlled medium of No. 408-8 squared paper sold by the American Pad & Paper Co.

The purpose of controlling the viscosity and penetration rate is to insure, in the case of the developer solution, that an optimum film thickness is maintained on the surface of the medium, while in the case of the liquid reagent solution, that it quickly penetrates to permit the fingerprint colorant product to be formed within the matrix of the medium. The actual film thickness for the liquid developer will have a maximum thickness of 15 microns and for a 6.5 $cm^2$ pad will correspond to roughly 10 mg of liquid developer. The minimum thickness will be approximately 1 micron based on a weight measurement calculation of minimum mass per unit area to produce an acceptable fingerprint. The liquid reagent deposits roughly between 20 mg and 30 mg per 6.5 $cm^2$.

The derivation of the measured film thickness was accomplished by a subjective determination of an acceptable print range by empirical experiment since it is believed that objective standards have not been established at the present time. The actual values were determined from a weight measurement with a micro-balance. A control medium was measured initially by itself and remeasured after depositing the actual fingerprint.

Magnification of the thumb ridge structure at 50x discloses that a cross-section ridge pattern has basically a sinusoidal shape with the depth of the valleys varying in adults from approximately 80 to 230 microns. By providing a coating thickness range of the liquid developer solution within the parameters of 15 microns to 1 micron for a time period of approximately 20 seconds, it is possible to insure an adequate coating adherence to the ridge structure of the fingerprint to provide a clear and acceptable developed fingerprint.

Referring to FIG. 9, a graph of viscosity versus carrier solvent mixture ratios is disclosed for both the liquid developer solution and the liquid reagent solution. Curve 10 is the plot for a liquid developer solution of glycerine and saturated hydrated ferric chloride, while curve 12 is a plot of just glycerine and distilled water. Curve 14 is a plot of an ethylene glycol and sodium ferrocyanide solution, while curve 16 is a plot of an ethylene glycol and distilled water mixture. The operable parameters of viscosity and solution mixtures are noted on the graph.

Referring to FIG. 8, a graph of surface tension versus carrier solvent mixture ratios is disclosed for both the liquid developer inert carrier fluid and the liquid reagent inert carrier fluid. It is believed that the inclusion of the active chemicals will not vary the plot mixtures more than 10 percent.

The specific active reagents of the first developer solution and second reagent solution can be selected from a number of possible systems. In a preferred embodiment, an inorganic-inorganic system is utilized since it provides a resultant colorant product representative of the fingerprint ridge pattern which is relatively stable to light, e.g., ultraviolet energy, and is further stable over a long period of time, apparently, because of the stronger ionic bonding that can be created as opposed to the covalent bonding in the prior art organic chemical systems. The inorganic-inorganic system is also more stable to heat and is not as susceptible to dissolving, or bleeding, in oils or solvents.

In the preferred embodiment, the active components of the liquid developer solution and the liquid reagent solution are respectively water soluble inorganic compounds which are capable of reacting to form a colorant product. Preferably, the product will be a non-soluble colorant precipitate. The first liquid developer solution can be a mixture of hydrated ferric chloride, water and glycerine having a viscosity range between 20 and 100 cps and a steady state penetration rate of 1.7 microns/sec. The volume mixture of the first liquid developer solution will contain 15 to 55 percent saturated hydrated ferric cloride and 45 to 85 percent glycerine. The 15 to 55 percent saturated hydrated ferric cloride being at a room temperature of 20° C. A volume mixture ratio of 33 percent saturated hydrated ferric cloride and 67 percent glycerine has provided excellent results.

The second reagent liquid solution can be a mixture of sodium hexacyanoferrate (11) decahydrate (sodium ferrocyanide), distilled water and ethyleneglycol having a viscosity in the range of 5 to 10 cups and a steady state penetration rate of 8 microns/sec. The second liquid reagent solution includes a volume mixture of approximately 33 percent sodium hexacyanoferrate (11) decahydrate and distilled water and 67 percent ethylene glycol. An operative reagent solution can include a volume mixture in the range of 20 to 50 percent sodium hexacyanoferrate (11) decahydrate and a volume mixture in the range of 50 to 80 percent ethylene glycol. The approximate concentration of sodium hexacyanoferrate (11) decahydrate is 10 grams to 50 millimeters of water. The reaction formula can be set forth as follows:

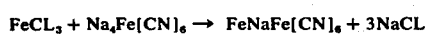

$FeCL_3 + Na_4Fe[CN]_6 \rightarrow FeNaFe[CN]_6 + 3NaCL$

Alternatively, it is possible to use potassium ferricyanide $(K_3FE(CN)_6$ or potassium ferrocyanide. The resultant colorant precipitate of the potassium compound will have the characteristics Prussian blue or Turnbull's blue color with a fast reaction time. The preferred embodiment of ferric chloride and sodium hexacyanoferrate (11) decahydrate has an advantage of providing an intense color precipitate with a fast reaction time while being relatively non-toxic to the user. These characteristics are important in being able to distinguish ridge endings, curves, and ridge bifurcations or minutiae of the person's fingerprint and to be sure that the print is not blurred when taken.

Another embodiment of an inorganic-inorganic reactant system is hydrogen peroxide/potassium iodide in a soluble starch solution. It is possible for the iodides to react with a number of oxidizing agents to yield a free iodide in the presence of starch which will provide a deep blue adsorption compound. For example, a 3 percent by volume hydrogen peroxide solution would mix with water as the developer solution and, appropriately, chemically react with a reagent solution of 10 by weight potassium iodide and 10 percent by weight soluble starch in distilled water. The resulting reaction formula can be set forth as follows:

$2KI + H_2O_2 \rightarrow I_2 + 2KOH$ wherein the fingerprint ridge pattern will be a blue, or brown, depending on the concentration.

It is also possible to uitilize an inorganic-organic system as the active chemical components of the developer and reagent solutions. A basic general reaction formula can be set forth as follows with a ferric salt:

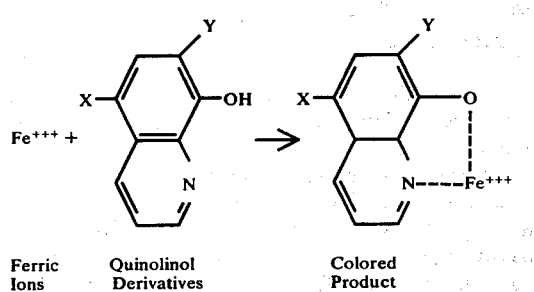

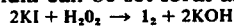

| Ferric | Quinolinol | Colored |
| Ions | Derivatives | Product |

Various forms of salts of transition metals can be utilized as a developer solution, such as salts of Iron, Titanium, Vanadium, Chromium, Magnesium, Cobalt, Nickel, Copper, Zironium, Niobium, Molybdenum, Silver, Tantalum and Tungsten. It is also possible to use Citrate, Sulfate, Ammonium Sulfate, Chloride, Bromide, Iodide, Nitrate, Stearate, Oleate, Borate, Acetate, Chlorate, Formate, Lactate, Maleate, Phosphate, and Tartrate salts of the above transition metals as the developer.

The reagent solution can include as the active ingredient 8-Hydroxy-quinoline derivatives where X and Y can be any of the following pairs of groups on the basic 8-Hydroxy-quinoline structure:

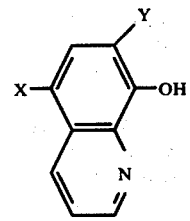

| X | Y |
| --- | --- |
| H | H |
| SO$_3$H | SO$_3$H |
| SO$_3$H | H |
| H | SO$_3$H |
| SO$_3$H | I |
| SO$_3$H | Br |
| SO$_3$H | Cl |
| Br | Br |
| Br | SO$_3$H |
| Cl | Cl |
| I | I |
| SO$_3$H | NO$_2$ |
| NO$_2$ | SO$_3$H |

Examples of chemical coumpounds which can be utilized as reagents are as follows:

2,4,6-Trihydroxy Benzoic Acid
3,4,5-Trihydroxy Benzoic Acid
Dimethyl Glyoxime Rubeanic Acid
Potassium Ferrocyanide
Sodium Ferrocyanide
Pyrogallol
Hydroquinone
Pyrocatechol
Propyl Gallate
Resorcinol
β-Resorcylic Acid
Tiron (4,5-Dihydroxy-m-Benzene Disulfonic Acid Disodium Salt)
Gentisic Acid
Procatechuic Acid
Phloroglucinol
Tannic Acid An example of one embodiment of the inorganic-organic system is a ferric chloride developer with a saturated aqueous solution of the sodium salt of 8-Hydroxy-5Quinolinol sulfonic acid in ethylene glycol as the reagent. The chemical reaction can be set forth as follows:

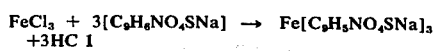

$FeCl_3 + 3[C_9H_6NO_4SNa] \rightarrow Fe[C_9H_5NO_4SNa]_3 + 3HCl$

It is also possible to utilize a pH sensitive system wherein the liquid reagent solution will include an active chemical capable of changing color when subjected to a change in pH, generally within the range of 4 to 10. known in the art, pH is a measure of the hydrogen ion concentration. The liquid developer will be a chemical compound having a sufficiently different pH value from that of the liquid reagent to effectuate a distinct color change.

| Reagent | Color Change | pH Range | Developer |
|---|---|---|---|
| Ethyl Bis(2,4-Dinitrophenyl) Acetate | colorless to blue | 8.5–9.5 | Sodium Carbonate |
| Ethyl Red | colorless to red | 4–6 | Asetic or Citric Acid |
| O-Cresolphthalein | colorless to red | 8–10 | Sodium Carbonate |
| Bromothymol Blue | yellow to blue | 6–7.5 | Sodium Carbonate |
| Chlorophenol Red | yellow to red | 5.2–7 | Sodium Carbonate |
| Thymol Blue | yellow to blue | 8–9 | Sodium Carbonate |

Other examples of developer agents for a pH system are Sodium Bicarbonate, Tartaric Acid, Calcium Hydroxide, Magnesium Hydroxide, and Sodium Hydroxide.

The above active chemical ingredients are simply suggestive of possible systems that can be utilized in the applicator of the present invention and should not be considered limiting to the generic principles and teachings of the present invention. The particular amount of individual chemicals required to be intermixed with the specific inert carrier fluids described herein can be easily determined by an artisan given the design parameters set forth herein of the present invention. Accordingly, the specific ratios are not required to be set forth.

Referring to FIGS. 6 and 7, an exploded view of the fingerprint applicator apparatus 2 of the present invention designed to accommodate replaceably cartridges is disclosed. A cap 20 can carry an appropriate indicia or information and is attached to a knob, or handle, 22. A compression spring 24 is mounted between a housing 26 and the knob 22 to bias the knob away from the housing 26. A shaft 28 having a tubular rivet end 30 is attached to the knob 22. The upper portion of the shaft 28 has a straight knurl to prevent rotation and the attachment of the shaft 28 is accomplished by peening over the tubular rivet end 30 onto the knob 22. The outer end of the shaft 28 is threaded and has a transverse bore for receiving a roll pin 34 to act as a knob spring retainer whenever a cartridge is removed.

A cartridge top plate 36 has a series of anti-rotation ribs 38 and is attached to a foam pad, or sponge, 40. The foam pad 40 provides a resilient give between the application of the force on the knob 22 and the contact of the respective chemical pads on the medium surface. The cartridge top plate 36 further carries a pair of prongs 42 which are designed to extend through clearance holes 44 in the foam pad 40. A cartridge body 46 has a pair of holes 48 designed to receive the prongs 42.

As can be seen with more particularity in FIG. 7, the external housing of the cavity 26 has a pair of anti-rotation ribs 50 designed to cooperate and coact with the anti-rotation ribs 38 on the cartridge top plate 36 to prevent rotational movement between the cartridge and the housing. The cartridge body is split into three sections to receive respectively a first and second chemical pad 52 and 54, and an ink pad having appropriate indicia 56. The respective pads are secured to the cartridge body 46 and the cartridge body can receive a plastic cartridge cover 58 to protect the respective pads. The individual components, apart from the pads, can be formed from plastic or metal.

Referring specifically to FIG. 5, a cross-sectional view of an assembled applicator assembly 2 is disclosed in a passive state. In use, the peripheral edge of the housing 26 will contact the medium surface and a depression of the knob 22 will force the cartridge body 46 downward against the bias of spring 24 to permit the respective chemical pads 52 and 54, and the ink pad 56 to contact the medium surface. The resilient sponge 40 assists in providing an appropriate pressure and in equalizing the application of force to the respective pads.

In the embodiment disclosed in FIGS. 5, 6, and 7, the cartridge body 46 is attached to the cartridge top plate 36 through a pair of prongs 42. When replacing the cartridge, the knob 22 is rotated and the cartridge top plate 36 is unthreaded from the shaft 28. Obviously, other forms of latching mechanisms can be utilized for removably attaching a cartridge to the housing. For example, various forms of springs, detents, latch mechanisms, etc. may be utilized for effectuating a removable connection with the housing. Accordingly, the present invention should not be limited to any particular form of latching mechanism for the removable cartridge with the applicator housing.

Referring specifically to FIG. 1, the applicator apparatus 2 is disclosed after it has contacted the medium surface and deposited the developer and reagent solution. Because the developer solution has a low interfacial surface tension and a relatively high viscosity, its penetration rate into the medium will be retarded and a useable film thickness will be maintained for approximately 20 seconds. The person whose fingerprint is to be taken will firmly press his finger against the coated liquid developer medium to adequately coat the ridge pattern of his finger. This process step is disclosed in FIG. 2

Referring to FIG. 3, the next process step of contacting the finger with the coated ridge pattern onto the reagent solution to permit a chemical reaction for producing a colorant product in the matrix of the paper, is disclosed. In FIG. 4, the resultant fingerprint which is developed immediately is disclosed and forms a permanent record that is integral with the medium. Accordingly, the medium, such as a check, is provided with a positive form of identification that cannot be erased in any subsequent electronic processing of the check.

Referring to FIG. 7, the respective chemical pads 52 and 54 can be formed of an open-foam cell resilient material that can have a pressurized heat sealed surface with a limited number of pores. One embodiment of the present invention utilizes a resilient pad with pore size in the range of 1 to 5 microns with the number of the proes on the surface being approximately $0.5 \times 10^{+6}$ per square inch. A resilient foam pad of this form is capable of keeping the first liquid developer solution and the second liquid reagent solution in a relatively non-evaporative state when the housing rests on a planar surface, while exposed to ambient conditions. Other types of resilient pads can be utilized, both for the pads 52 and 54, and further, for the ink pad 56.

The applicator of the present invention as disclosed in FIGS. 5, 6, and 7, can be varied within the principles of the present invention to provide other highly advantageous forms. As illustrative of another embodiment of the present invention, reference is made to FIG. 10 which discloses a hand operated printing machine particularly adapted to receive credit cards. As can be readily appreciated, the theft and misuse of credit cards is a major problem. The printing machine 60 includes a bed 62 which can be stamped to form a top plate 64 having a pair of wells 66 and 68. Mounted respectively within the wells 66 and 68, are resilient pads 70 and 72. Each resilient pad is adapted to carry a respective liquid developer solution and liquid reagent solution in accordance with the previously set forth design parameters of the present invention. Alternatively, the respective resilient pads 70 and 72 can be jointly mounted in a cartridge (not shown) with appropriate design modifications to the bed 62 to receive a replaceable cartridge.

The bed 62 is also designed to accommodate a credit card and, for example, a dater wheel assembly 74 as known in the prior art. Also, as known in the prior art, impressions are produced on an appropriate medium by a platen roller that can be rotatably supported in a carriage 76 that is movable across the bed 62. The improvement to the prior art printing machine is established by including the resilient pads 70 and 72 so that the platen roller can force an appropriate medium, such as the credit card receipt slip, against the respective resilient pads to deposit a desired amount of the liquid developer solution and liquid reagent solution on the reverse side of the credit card receipt. The credit card receipt can then be presented to the purchaser so that he can then provide a positive form of identification with his fingerprint on the credit card receipt.

The particular printing machine 60 can take many different forms and reference is made herein to the Maul et al., U.S. Pat. No. 3,018,725; and the Maul, U.S. Pat. No. 3,138,091 to disclose two conventional forms of printing machines. The disclosure of these patents are incorporated herein by reference to supplement the present disclosure.

The embodiment of the invention disclosed in FIG. 10 illustrates the advantages of the present invention of depositing directly on the medium, both the liquid developer solution and the liquid reagent solution in one convenient process step. As can be readily imagined, other forms and embodiments of the present invention are capable within the generic principles set forth herein, and accordingly, the scope of the present invention should be measured solely from the following claims:

What is claimed is:

1. Identification apparatus for preparing a porous medium, such as a check and the like, to retain an identifiable fingerprint comprising:
    first means for applying a quanitity of a first liquid developer solution to the medium, the developer solution as applied having sufficient film thickness on the porous medium to contact and adhere to substantially only the ridge pattern of a finger when the finger is applied to the coated medium; and
    second means for applying a quanitity of a second liquid reagent solution to the medium, the second liquid reagent having a significantly higher penetration rate into the medium than the first liquid developer solution, the first liquid developer solution and second liquid reagent solution capable of chemically interacting to provide a perceivable coloraant product representative of a fingerprint ridge pattern whereby a finger can be first applied to the liquid developer coating on the medium to coat substantially only the ridge pattern and then subsequently applied to the liquid reagent on the medium to provide a colorant product representative of the fingerprint ridge pattern.

2. The invention of claim 1 wherein the first and second means are resilient pads.

3. The invention of claim 1 further including a housing operatively connected to the first and second means for applying the respective developer solution and reagent solution to the medium.

4. The invention of claim 3 wherein the housing further includes printing means for printing indicia on the medium adjacent the first and second applying means.

5. The invention of claim 3 wherein the first and second applying means are resilient pads attached to a cartridge housing, the cartridge housing being removably attached to the housing.

6. The invention of claim 5 wherein the first and second means are resilient foam pads with a partially porous membrance covering.

7. The invention of claim 1 wherein the first liquid eveloper solution is a mixture of hydrated ferric chloride, water and glycerine.

8. The invention of claim 1 wherein the second liquid reagent solution is a mixture of sodium hexacyanoferrate (II) decahydrate, water and ethylene glycol.

9. The invention of claim 7 wherein the viscosity of the first liquid developer is in the range of 20 to 100 cps and the viscosity of the second liquid reagent solution is in the range of 10 to 5 cps.

10. The invention of claim 9 wherein the first liquid developer solution consists of a volume mixture in the range of 15 to 55 percent saturated hydrated ferric chloride in water at approximately 20° C with a volume mixture of 45 to 85 percent glycerine.

11. The invention of claim 8 wherein the second liquid reagent solution includes a volume mixture of approximately 33 percent sodium hexacyanoferrate (II) decahydrate and water and 67 percent ethylene glycol.

12. The invention of claim 11 wherein the approximate concentration of sodium hexacyanoferrate (II) decahydrate is 10 grams to 50 ml of water.

13. The invention of claim 1 wherein the liquid developer solution and the liquid reagent solution are respectively water soluble inorganic compounds which can react to form a non-soluble colorant precipitate.

14. The invention of claim 1 wherein the liquid developer solution and the liquid reagent solution are respectively a ferric salt solution and a quinolinol derivative solution.

15. The invention of claim 1 wherein the liquid developer solution includes a salt compound selected from the group consisting of Chromium, Copper, Vanadium, Manganese, Titanium, Cobalt, Iron, Nickel, Zirconium, Niobium, Molybdenum, Silver ,Tantalum and Tungsten.

16. The invention of claim 1 wherein the isobaric penetration rate of the first liquid developer solution is approximately in the range of 1 to 2 microns/sec and the isobaric penetration rate of the second liquid reagent solution is approximately in the range of 6 to 10 microns/sec, the respective penetration rates being measured in a porous medium of No. 408 paper.

17. The invention of claim 14 wherein the liquid reagent solution is an 8 Hydroxy-quinoline derivative having the following structure:

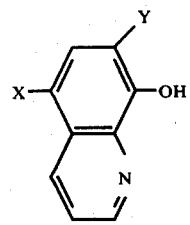

where X and Y can be selected from any one of the following pairs of groups:

| X | Y |
|---|---|
| H | H |
| SO₃H | SO₃H |
| SO₃H | H |
| H | SO₃H |
| SO₃H | I |
| SO₃H | Br |
| SO₃H | Cl |
| Br | Br |
| Br | SO₃H |
| Cl | Cl |
| I | I |
| SO₃H | NO₂ |
| NO₂ | SO₃H |

18. The invention of claim 2 wherein the respective resilient pads are open foam celled and have a sealed surface with a limited number of pores compared to the number of cells.

19. The invention of claim 18 wherein the pore size is in the range of 1 to 5 microns and the number of pores are approximately $0.5 \times 10^6$ pores/square inch.

20. The invention of claim 5 wherein the first liquid developer solution and the second liquid reagent solution when contained in their respective pads, are relatively non-evaporative when the housing rests on a planar surface while exposed to ambient conditions.

21. The invention of claim 1 wherein the liquid reagent solution and the liquid developer solution include respectively a chemical compound having a pH in the range of 4 to 10 and a chemical compound which effectuates a distinct color change within this range.

22. The invention of claim 5 further including a manually operable member, a shaft member connected to the operable member and the cartridge housing; and means for biasing the operable member away from the housing whereby a force exerted on the operable member permits the cartridge housing to move relative to the housing when the housing is held stationary.

23. The invention of claim 22 further including spring means connected between the shaft and the cartridge housing to permit relative movement.

24. The invention of claim 1 wherein the isobaric penetration rate of the second liquid reagent solution is approximately three times greater than the first liquid developer solution.

25. The invention of claim 24 wherein the viscosity of the first liquid developer is at least twice that of the second liquid reagent solution.

26. The invention of claim 25 wherein the first liquid developer solution includes a mixture of hydrated ferric chloride, water and glycerine and the second liquid reagent solution includes at least a mixture of sodium hexacyanoferrate (II) decahydrate, water and ethylene glycol.

27. In an identification apparatus for respectively preparing a medium, such as checks, paper documents and the like, to be used in a two-step printing process to retain identifiable indicia in the medium having a housing the improvement including a replaceable cartridge for attachment to the housing comprising:

at least a pair of reservoir resilient pads operatively attached to the cartridge for pressure contact with the surface of the medium;

a first liquid developer solution contained in one pad, the pad, upon pressure contact with the medium surface, depositing a quantity of the first liquid developer solution to provide a coating having only sufficient thickness above the medium surface to contact and adhere to substantially only a raised surface pattern; and a second liquid reagent solution contained in the other pad having a viscosity value of not more than half the viscosity value of the first liquid developer solution, the second reagent solution also being applied and absorbed into the medium upon pressure contact, the second liquid reagent solution having an isobaric penetration rate into the medium at least twice as great as the isobaric penetration rate of the first liquid developer solution, the reagent liquid capable of chemically interacting with the developer solution to provide an immediate colorant precipitate in the medium, the respective pads applying the first liquid developer solution and the second liquid reagent solution directly to the medium, whereby indicia is developed by the sequential contact of the raised surface pattern to the deposited solutions.

28. The invention of claim 27 wherein the liquid developer solution and the liquid reagent solution are respectively water soluble inorganic compounds which can react to form a non-soluble colorant precipitate.

29. The invention of claim 27 wherein the liquid developer solution and the liquid reagent solution are respectively a ferric salt solution and quinolinol derivative solution.

30. The invention of claim 28 wherein the first liquid developer solution is a mixture of ferric chloride, water and glycerine.

31. The invention of claim 30 wherein the second liquid reagent solution is a mixture of sodium hexacyanoferrate (II) decahydrate, water and ethylene glycol.

32. The invention of claim 28 wherein the first liquid developer solution consists of a volume mixture in the range of 15 to 55 percent saturated hydrated ferric chloride in water at approximately 20° C complementing a volume mixture of 45 to 85 percent glycerine.

33. The invention of claim 32 wherein the second liquid reagent solution includes a volume mixture in the range of 20 to 50 percent sodium hexacyanoferrate (II) decahydrate and water and a volume mixture in the range of 50 to 80 percent ethylene glycol.

34. The invention of claim 33 wherein the approximate concentration of sodium hexacyanoferrate (II) decahydrate is 10 grams to 50 ml of water.

35. The invention of claim 27 wherein the isobaric penetration rate of the first liquid developer solution is approximately in the range of 1 to 2 microns/sec and the isobaric penetration rate of the second liquid reagent solution is approximately in the range of 6 to 10 microns/sec, the respective penetration rates being measured in a porous medium of No. 408 paper.

36. The invention of claim 27 wherein the liquid developer solution and the liquid reagent solution are respectively a metallic salt solution and an 8 Hydroxy quinoline derivative solution.

37. The invention of claim 27 wherein the liquid reagent solution and the liquid developer solution include respectively, a chemical compound having a pH in the range of 4 to 10 and a chemical compound having a sufficiently different pH to effectuate a distinct color change.

38. The invention of claim 27 wherein the first liquid developer solution comprises a volume mixture in the range of 15 to 55 percent saturated hydrated ferric chloride in water at approximately 20° C complementing a volume mixture of 45 to 85 percent glycerin, and the second liquid reagent solution includes a volume mixture in the range of 20 to 50 percent sodium hexacyanoferrate (II) decahydrate and water and a volume mixture in the range of 50 to 80 percent ethylene glycol wherein the approximate concentration of sodium hexacyanoferrate (II) decahydrate is 10 gms to 50 ml of water.

39. A substantially stainless fingerprint identification apparatus for preparing a porous medium, such as a check, paper document and the like, for developing and retaining an identifiable fingerprint in the medium comprising:

first means for applying a quantity of a first liquid developer solution to the medium, the developer solution as applied maintaining for a limited time period sufficient film thickness on the porous medium to contact and adhere to substantially only the ridge pattern of a finger when the finger is applied to the coated medium; and second means for applying a quantity of a second liquid reagent solution to the medium, the second liquid reagent solution having an isobaric penetration rate at least twice as great as the isobaric penetration rate of the first liquid developer solution, to thereby penetrate into the medium while the first liquid developer solution is still on the medium surface, the first liquid developer solution and second liquid reagent solution capable of chemically interacting in the medium when intermixed to provide a permanent perceivable colorant product representative of a fingerprint ridge pattern in the medium while substantially not leaving any staining colorant product on the finger, whereby a finger can be first applied to the liquid developer coating on the medium to coat substantially only the fingerprint ridge pattern and then subsequently applied to the liquid reagent on the medium to provide a colorant product representative of the fingerprint ridge pattern.

40. The invention of claim 39 wherein the respective active chemical components of the first liquid developer solution and the second liquid reagent solution are inorganic.

41. The invention of claim 40 wherein the viscosity of the first liquid developer is at least twice that of the second liquid reagent solution.

42. The invention of claim 41 wherein the first liquid developer solution includes a mixture of hydrated ferric chloride, water and glycerine and the second liquid reagent solution includes at least a mixture of sodium hexacyanoferrate (II) decahydrate, water and ethylene glycol.

43. The invention of claim 42 further including a cartridge housing, a housing operatively connected to the first and second means for applying the respective liquid developer solution and liquid reagent solution to the porous medium, the first and second applying means including resilient pads attached to the cartridge housing, the cartridge housing being removably attached as a unit to the housing;

44. The invention of claim 43 further including a manually operable member, a shaft member connected to the operable member and the cartridge housing, and means for biasing the operable member away from the housing whereby a force exerted on the operable member permits the cartridge housing to move relative to the housing when the housing is held stationary.

45. The invention of claim 44 further including resilient means connecting the shaft and the cartridge housing to permit relative movement during the application of solutions to the medium.

* * * * *

UNITED STATES PATENT AND TRADEMARK OFFICE
CERTIFICATE OF CORRECTION

PATENT NO. : 4,029,012
DATED : June 14, 1977
INVENTOR(S) : Jay Smith III and Virgle L. Hedgcoth It is certified that error appears in the above-identified patent and that said Letters Patent are hereby corrected as shown below:

Col. 1, line 22 delete "and" and insert --an--.
       line 29 after "has" insert --readily--.
       line 53 delete "finer" and insert --finger--.
       line 57 delete "pattern" and insert --patterns--.

Col. 2, line 48 delete "T432ts-64" and insert --T432-ts-64--.

Col. 3, lines 29 and 30 delete "obtained" and insert --contained--.

Col. 4, line 21 after "is" insert --a--.

Col. 5, line 46 after "active component" insert --that is complementary to the active component--.

Col. 5, line 68 delete "commercail enviroment" and insert --commercial environment--.

Col. 6, line 22 delete "undersirable" and insert --undesirable--.

Col. 9, line 3 delete "ethyleneglycol" and insert --ethylene glycol--.

Col. 9, line 4 delete "cups" and insert --cps--.
       line 15 delete "millimeters" and insert --milliliters--.

Col. 9, line 21 delete "$(K_3FE(CN)_6$" and insert --$(K_3F_e(CN)_6)$--.

Col. 9, line 41 after "10" insert --percent--.

UNITED STATES PATENT AND TRADEMARK OFFICE
CERTIFICATE OF CORRECTION

PATENT NO. : 4,029,012
DATED : June 14, 1977
INVENTOR(S) : Jay Smith III and Virgle L. Hedgcoth It is certified that error appears in the above-identified patent and that said Letters Patent are hereby corrected as shown below:

Col. 9, line 67 delete "Zironium" and insert --Zirconium--.

Col. 10, line 36 delete "Rubeanic Acid" insert on separate line after Dimethyl Glyoxime --Rubeanic Acid--.

Col. 10, line 65 insert --As-- before "known".

Col. 11, line 27 delete "an" and insert --any--.
line 36 delete "outer" and insert --other--.

Col. 12, line 46 delete "proes" and insert --pores--.

Col. 13, line 56 delete "coloraant" and insert --colorant--.

Col. 14, line 10 delete "membrance" and insert --membrane--.

Col. 14, line 12 delete "eveloper" and insert --developer--.

Col. 16, line 17 delete "firstliquid" and insert --first liquid--.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks